United States Patent
Gaignon et al.

(10) Patent No.: US 10,639,156 B2
(45) Date of Patent: May 5, 2020

(54) SYNTHETIC BLOCK INTENDED FOR FILLING IN A BONE DEFECT AND METHOD FOR MANUFACTURING SAME

(71) Applicant: 3DCERAM, Limoges (FR)

(72) Inventors: Richard Gaignon, Saint-Vrain (FR); Christophe Chaput, Le Palais sur Vienne (FR)

(73) Assignee: S.A.S. 3DCERAM-SINTO, Limoges (FR)

( * ) Notice: Subject to any disclaimer, the term of this patent is extended or adjusted under 35 U.S.C. 154(b) by 111 days.

(21) Appl. No.: 15/517,562

(22) PCT Filed: Oct. 12, 2015

(86) PCT No.: PCT/FR2015/052748
§ 371 (c)(1),
(2) Date: Apr. 7, 2017

(87) PCT Pub. No.: WO2016/055752
PCT Pub. Date: Apr. 14, 2016

(65) Prior Publication Data
US 2017/0304056 A1    Oct. 26, 2017

(30) Foreign Application Priority Data

Oct. 10, 2014   (FR) ...................................... 14 59765

(51) Int. Cl.
| | |
|---|---|
| *A61F 2/28* | (2006.01) |
| *A61L 27/10* | (2006.01) |
| *A61L 27/12* | (2006.01) |
| *A61L 27/56* | (2006.01) |
| *A61F 2/30* | (2006.01) |
| *A61L 27/58* | (2006.01) |
| *A61B 17/86* | (2006.01) |

(52) U.S. Cl.
CPC ........ *A61F 2/2803* (2013.01); *A61F 2/30942* (2013.01); *A61L 27/10* (2013.01);
(Continued)

(58) Field of Classification Search
CPC .................. A61F 2/2803; A61F 2/2846; A61F 2002/2835; A61F 2002/30011;
CPC . A61F 2002/30013; A61F 2002/30578; A61L 27/56; A61L 27/58; A61L 27/10
See application file for complete search history.

(56) References Cited

U.S. PATENT DOCUMENTS

| | | | |
|---|---|---|---|
| 2005/0085922 A1 | 4/2005 | Shappley et al. | |
| 2010/0256773 A1* | 10/2010 | Thijs .................... | A61C 8/0006 623/23.55 |

FOREIGN PATENT DOCUMENTS

| | | |
|---|---|---|
| JP | 54-155695 A | 12/1979 |
| JP | 2010-531694 A | 9/2010 |

(Continued)

OTHER PUBLICATIONS

Thavornyutikarn et al., Bone tissue engineering scaffolding: computer-aided scaffolding techniques, Jul. 17, 2014, Prog Biomater 3: 61-102 (Year: 2014).*

(Continued)

*Primary Examiner* — Brian A Dukert
(74) *Attorney, Agent, or Firm* — Young & Thompson

(57) ABSTRACT

Disclosed is a synthetic block intended for filling in a bone defect. The block is made up of a part made of ceramic material which has a shape that enables same to fill in the bone defect, and which is capable of being stabilized once placed in the bone defect, a three-dimensional network of channels communicating with one another being formed at least partially in the part such as to allow through the fluids and cells that enable revascularization with a view to cell growth once the part is in place in the bone defect, the channels opening onto each surface of the bone defect in contact with the part once it is placed in the bone defect.

26 Claims, 4 Drawing Sheets

(52) U.S. Cl.
CPC ............ *A61L 27/12* (2013.01); *A61L 27/56* (2013.01); *A61L 27/58* (2013.01); *A61B 17/86* (2013.01); *A61F 2002/30011* (2013.01); *A61F 2002/30062* (2013.01); *A61F 2002/3092* (2013.01); *A61F 2002/30578* (2013.01); *A61F 2002/30772* (2013.01); *A61F 2002/30784* (2013.01); *A61F 2002/30962* (2013.01); *A61F 2002/30985* (2013.01); *A61F 2310/00293* (2013.01); *A61L 2430/02* (2013.01)

(56) References Cited

FOREIGN PATENT DOCUMENTS

| WO | 2009/004070 A1 | 1/2009 |
| WO | 2009/129000 A2 | 10/2009 |
| WO | 2013/181375 A1 | 12/2013 |

OTHER PUBLICATIONS

Ebrahimi et al., Fabrication and characterization of novel nano hydroxyapatite/B-tricalcium phosphate scaffolds in three different composition ratios, Apr. 12, 2012, Journal Biomed Material Res Part A 2012: 100A:2260-2268 (Year: 2012).*

Seitz et al., Three-Dimensional Printing of Porous Ceramic Scaffolds for Bone Tissue Engineering, Jun. 24, 2005, Journal of Biomedical Materials Research Part B, Applied Biomaterials, vol. 74B, Issue 2, pp. 782-788 (Year: 2005).*

International Search Report, dated Jan. 20, 2016, from corresponding PCT application.

FR Search Report, dated Jun. 2, 2015, from corresponding FR application.

Japanese Office Action issued in Application No. 2017-538465, dated Apr. 24, 2018 with English translation.

* cited by examiner

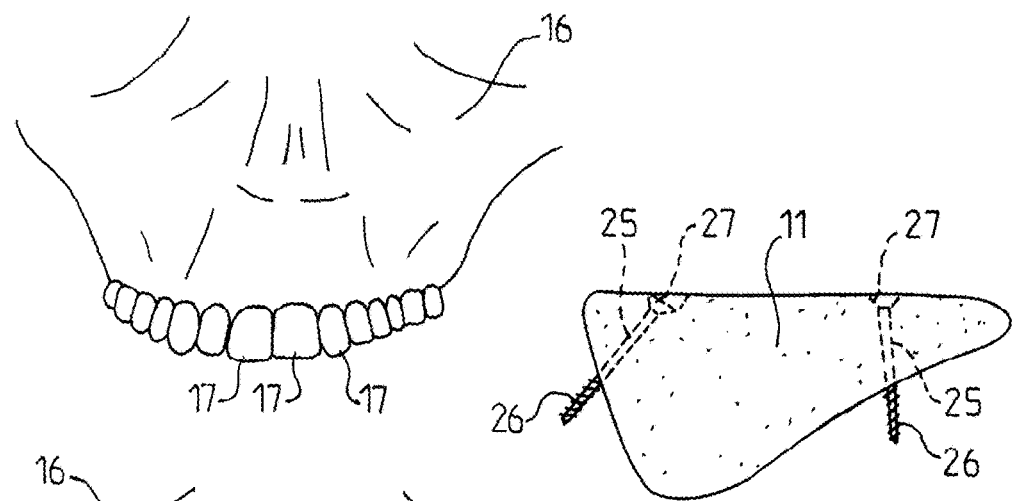
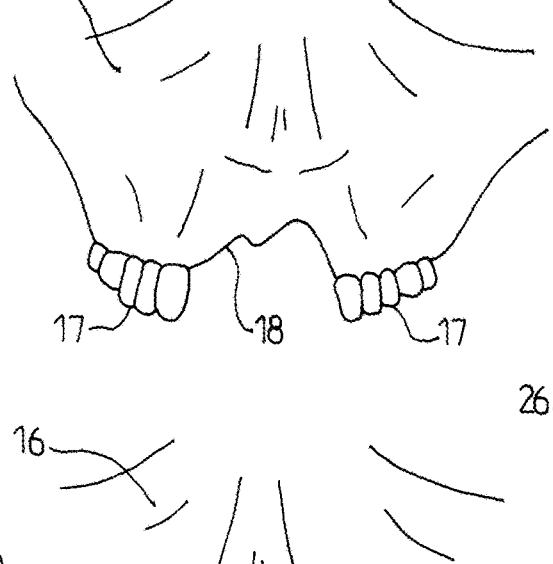
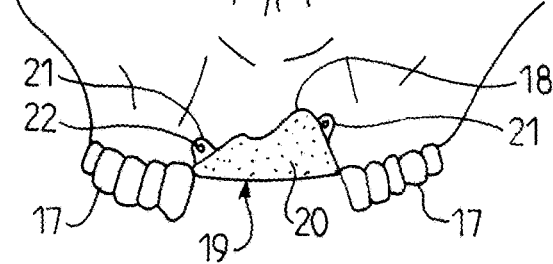
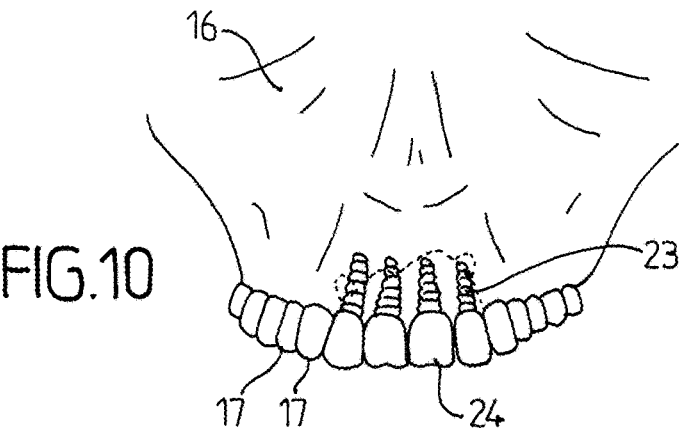
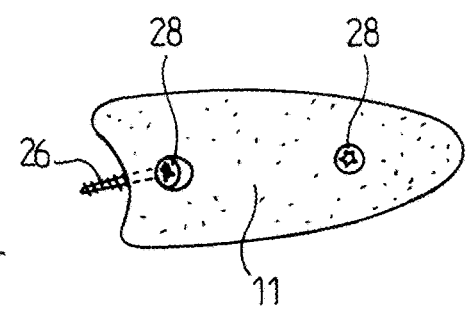
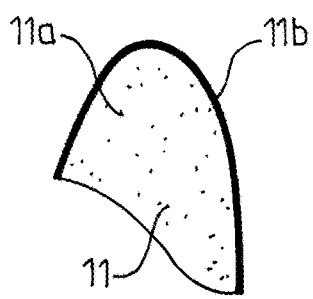

SYNTHETIC BLOCK INTENDED FOR FILLING IN A BONE DEFECT AND METHOD FOR MANUFACTURING SAME

The present invention relates to a synthetic block intended for filling in a bone defect at the surface of a bone, as well as a method for manufacturing said synthetic block.

Particularly, the treated bone defect according to the invention is a bone defect occurring within the bone of a mandible or a maxilla. However, the invention is not limited to such bone defects.

The bone volume of the maxillae is a critical data for placing implants, namely artificial roots for replacing missing teeth.

Currently, when the bone volume is insufficient, it is possible to:

use, for small volumes, filling products as pellets or paste of synthetic (β-tricalcium phosphate, hydroxyapatite), human or animal (bovine, porcine, equine) origin: such an application constitutes the Guided Bone Regeneration (GBR);

for large volumes, it is required to perform apposition grafts with blocks of human (bank bones), animal or synthetic origin, or with bone blocks of the patient being operated, autografted by symphyseal, ramic or parietal sampling.

These known techniques present difficulties since the above-mentioned blocks cause issues of shape and quantity. Indeed, they have a standard size and thus require to be intraoperatively resized (during the surgery) so as to adjust them to the bone defect in the best possible way.

It results in:

stability issues since the blocks and the bone defect are never perfectly fitted;

risks of fracture by tipping of the block at the time of osteosynthesis (screw attachment);

osteointegration issues (colonization of the block by bone cells and formation of neovessels) and, thus, rejection of the block;

excessively sharp edge issues with a risk of soft tissue injury (covering tissues, gum, epithelium, connective tissue), thus a poor tissue healing which is though essential; the sutures of the soft tissues should allow a full tight sealing without any tension to expect an osteointegration of the block;

for autografts, an additional issue of a second surgical site with consequences resulting therefrom (sampling at ramus, mandibular symphysis or under general anesthesia at the parietal bone or the hip);

for autografts, the issue of the quantity one is able to sample.

The present invention is intended to overcome these drawbacks.

To this end, according to the invention, it is suggested to perform, by the technique of additive methods—also called stereolithography or 3D printing—synthetic blocks made of ceramic material perfectly fitted to the bone defects of patients, allowing to solve the different difficulties encountered with the current techniques.

Indeed, being performed by 3D printing (stereolithography) from the scanner data from the patient (STL files), the block is perfectly fitted to the defect:

eliminating the intraoperative adjustment states, difficult and risky for the block;

eliminating the adjustment issue of the block to the bone defect;

providing a better quality junction, thus a tight contact between the block and the bone cells of the blood;

providing the block body with a sufficient "porosity" allowing a colonization by the bone cells and a neovascularization (production of new blood vessels);

placing wells at accurate locations for passing one or more stabilization screws (osteosynthesis); namely, the block should be reinforced at the bearing of the screw heads and the chamfer and the diameter of these holes is adjusted to the diameter of the screws to avoid creating a tension and fractures of the block when clamping thereof;

the composition of the block made of ceramic material is essential to provide a planned total or partial resorption of the block and its total or partial filling by the patient's newly formed bone; indeed, the operator should intervene again on the surgical site after the end of the complete bone healing in order to place the one or more implants for which the increase in bone volume of the mandible or maxilla was necessary;

the issues encountered with the autografts (second surgical site and sampled quantity) are obviously entirely excluded.

The present invention thus relates first to a synthetic block intended for filling in a bone defect at the surface of a bone, characterized in that it is made up of a ceramic material part which has a shape allowing it to fill in the bone defect and which is able to be stabilized when placed within said bone defect, a three-dimensional network of channels communicating with one another being at least partially formed within said part for allowing through the fluids and cells that enable revascularization for cell growth once said part is placed within the bone defect, said channels opening onto each surface of the bone defect in contact with said part once it is placed within the bone defect.

The three-dimensional network of channels is an ordered network, thus different from a group of open interconnected pores, such as described in WO 2009/004070 A1. The ordered network is obtained by stereolithography or 3D printing or technique of additive methods, allowing to control the network structure, while the group of open interconnected pores is random, thus not controllable. The part could thus be manufactured according to the desired revascularization. Moreover, the part could include networks of channels with different density (number of channels per $cm^2$ or $cm^3$).

Advantageously, the ceramic material is a ceramic material which is at least partially resorbable. The ceramic material can also be a non-resorbable ceramic material.

The ceramic material is namely selected among β-tricalcium phosphate (β-TCP), hydroxyapatite and mixtures thereof in any proportion, being particularly composed of, for 100 wt. %, 40-100 wt. % of hydroxyapatite and 0-60 wt. % of β-TCP. A common mixture consists in 60 wt. % of hydroxyapatite and 40 wt. % of β-TCP. The β-TCP is resorbable while the hydroxyapatite is not resorbable.

The three-dimensional network of channels can have any shape insofar as it allows the revascularization by penetration of fluids and cells necessary for this revascularization; particularly, the cubic mesh networks, the channels then extending along each of the ridges of the cubic mesh network.

The ceramic part can externally have, integral therewith, at least one stabilization eyelet intended to abut against the surface of the bone to be restored, outside said bone defect, said stabilization eyelet being not provided with revascularization channels and being pierced with at least one hole for passing at least one stabilization screw, and/or said ceramic part can be pierced with at least one through hole, from the surface intended to come into contact with the bone delimiting said bone defect to the free surface if one considers the position of the part placed within the bone defect, for passing at least one stabilization screw, said part being not provided with revascularization channels within the regions surrounding said hole at least in the neighbouring part of said free surface.

Advantageously, the part is not provided with revascularization channels within the region of its free surface if one considers its position placed within the bone defect.

The channels forming the revascularization system can have any section, for example circular, square, triangular, diamond-shaped, with shapes having the greatest number of angles (for example, cross-shaped). Particularly, the channels forming the revascularization system can have a square section which side is 250-600 µm with a 200 µm tolerance.

Generally, the revascularization channels can have a variable section, be rectilinear or not, and open or not at the opposite side of the surface of the part intended to come into contact with the bone defect since the structure of these channels is controlled.

Advantageously, the channels forming the revascularization system have a greater section within the region of the part intended to contact the bone delimiting the bone defect, namely being square-section channels with a 400-600 µm side with a 200 µm tolerance, the core channels of the part being square-section channels with a smaller side; alternatively, the density of the channels forming the revascularization system can be higher within the one or more regions of the part intended to contact the bone defect.

The ceramic material constituting the part has in particular an intergranular microporosity, measured by mercury porosimetry, of 5-30% in volume, the micropores having a size of 0.1-10 µm. This microporosity is proper to the ceramic material being manufactured.

It is interesting that:
the core of the part has a structure as close as possible to the "porous" and soft trabecular bone;
the outer periphery of the part (considered in its position placed within the bone defect) has a structure as close as possible to the characteristics of the cortical bone: dense and rigid; and
the portion of the part intended to come into contact with the patient's bone is very "porous" for allowing the fastest possible revascularization.

The term "porous" above-mentioned refers to the presence of the network of channels as defined above. Indeed, the outer periphery of the part has the same structure as the rest of the part, with the microporosity inherent to the manufacturing method.

The present invention also relates to a method for manufacturing a synthetic block as defined above, characterized in that it comprises the following steps:
acquiring a three-dimensional image of a patient's bone having the bone defect to be filled in;
designing, by computer-aided design, a computing model of the synthetic block which shape corresponds to the bone defect, which has the revascularization channels and which sizes are slightly larger than said bone defect so as to take into account the shrinkage of the ceramic when manufacturing the synthetic block;
changing this computing model of the synthetic block, by computer-aided design, to ensure the stabilization of said synthetic block within said bone defect; and
manufacturing the desired synthetic block by stereolithography or 3D printing or technique of additive methods.

The method for manufacturing the ceramic material part as defined above generally comprises the steps consisting in:
forming, on a rigid support or on a part being manufactured, a first thermosetting composition layer comprising at least one ceramic material and a photocurable monomer;
curing the first photocurable composition layer, by irradiation according to the pattern defined for said layer, forming a first stage;
forming, on the first stage, a second photocurable composition layer;
curing the second photocurable composition layer, by irradiation according to the pattern defined for said layer, forming a second stage;
optionally repeating said steps for providing a green part;
cleaning the green part for removing the non-cured composition;
optionally debinding the cleaned green part;
sintering the optionally debinded and cleaned green part, for providing the finished part.

In a particular embodiment of the method, the part is manufactured by liquid stereolithography, the photocurable composition being liquid and the rigid support being a platform immersed within a photocurable composition bath, and each of the photocurable composition layers is formed by lowering the platform within the photocurable composition bath such that the upper stage of the part being manufactured is lowered below the free surface of the photocurable composition, and each of the photocurable composition layers is cured by laser scanning of said free surface according to the pattern defined for said layer.

In another particular embodiment of the method, the porous structure is manufactured by pasty stereolithography the photocurable composition being pasty, and the photocurable composition being provided to the upper stage of the part being manufactured, and the photocurable composition being spread for forming each of the photocurable composition layers, and each of the photocurable composition layers is cured by laser scanning of said layer according to the pattern defined for said layer.

The present invention also relates to the use of a synthetic block as defined above or manufactured by the method as defined above as a synthetic block intended for filling in a bone defect of a mandible or maxilla.

To better illustrate the object of the present invention, several embodiments will be described below for indicative and non-limiting purposes, with reference to the attached drawings, in which:

FIGS. 7 to 10 are front views of a maxilla respectively in a healthy state; after losing the incisive block; after placing a synthetic block according to the first embodiment of the present invention; and after complete bone healing and placing the dental implants;

Figure 3:
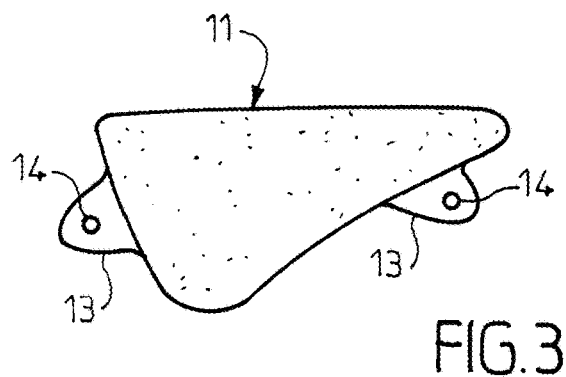
FIG. 3 is a side schematic view of a block intended for filling in this bone defect, the block being consistent with a first embodiment of the invention.
Figure 4:
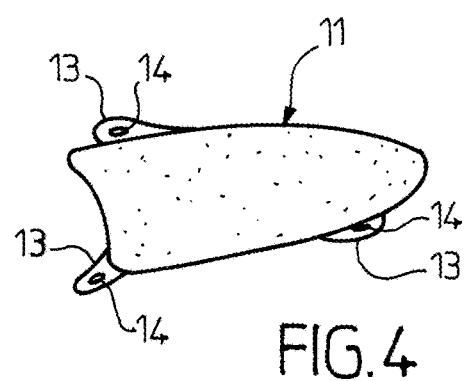
FIG. 4 is a top schematic view of the block of FIG. 3.
Figure 14:
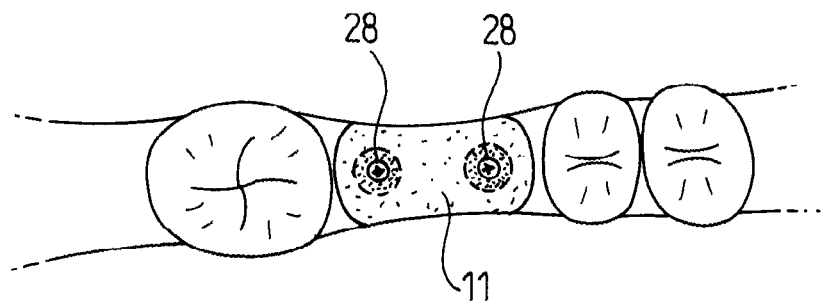
Figure 15:
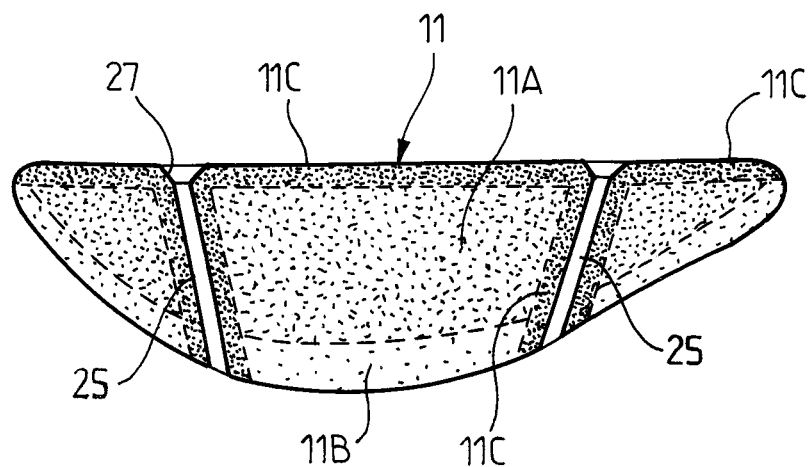

FIGS. 11 and 12 are views corresponding respectively to FIGS. 3 and 4, showing a synthetic block performed according to a second embodiment of the present invention, the fixation screws used with this second embodiment being shown on FIGS. 11 and 12;

FIG. 13 is a cross-sectional view of the synthetic block according to the first or second embodiment in order to describe a possible structure;

FIG. 14 is a top view of a mandible part comprising a bone defect filled in with a synthetic block consistent with the second embodiment of the invention; and FIG. 15 shows, on a larger scale, a longitudinal cross-sectional view of the synthetic block of FIG. 14, in order to describe the structure.

On the anatomic schematic views of the drawings, for clarity purposes, the soft tissues, such as gum, muscles and cheeks, and the vascular system are removed, while only the hard tissues, such as bones and teeth, remain.

Figure 1:
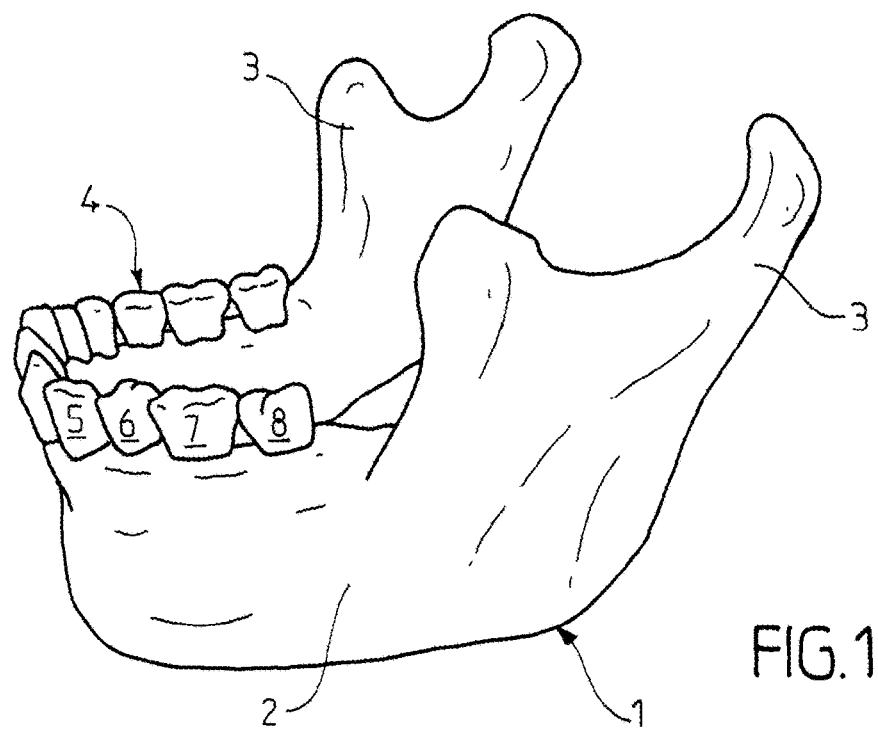
FIG. 1 is a perspective schematic view of the healthy mandible of an adult human being.

If referring to FIG. 1, it can be noted that the mandible 1 of an adult human being is shown, with its body 2 and its two branches 3. The body 2 carries the teeth 4 of the lower dental arch, the teeth being embedded within the drilled sockets within the spongy alveolar edge of the mandible body. On the drawing, the teeth are not shown accurately, the purpose of the invention being to represent a synthetic block intended for filling in a bone defect and its positioning therein. The teeth discussed here have been numbered by their position with respect to the middle of the mandible, namely: 5, second premolar; 6, first molar; 7, second molar; 8, third molar or wisdom tooth.

Figure 2:
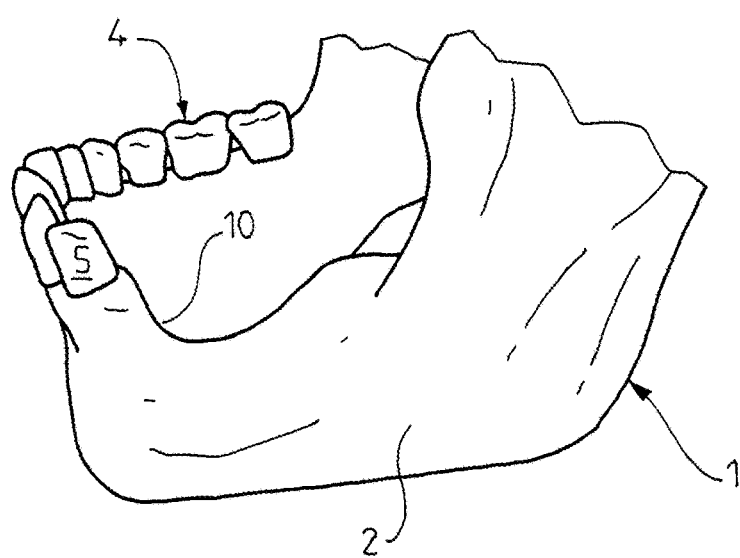
FIG. 2 is a view of the body of the mandible of FIG. 1 comprising a bone defect.

On FIG. 2 is shown the mandible body after losing the teeth 6, 7 and 8 and the associated alveolar bone.

The bone defect 10 thus formed is trough-shaped extending from a side wall to the other of the mandible body.

The ceramic material part 11 intended to fill in this defect 10 is shown on FIGS. 3 and 4.

It comprises a body 12 which has a shape allowing it to perfectly fit the defect 10, and which externally bears three eyelets 13 in the example shown, namely two eyelets on one side and one eyelet on the other side.

Figure 5:
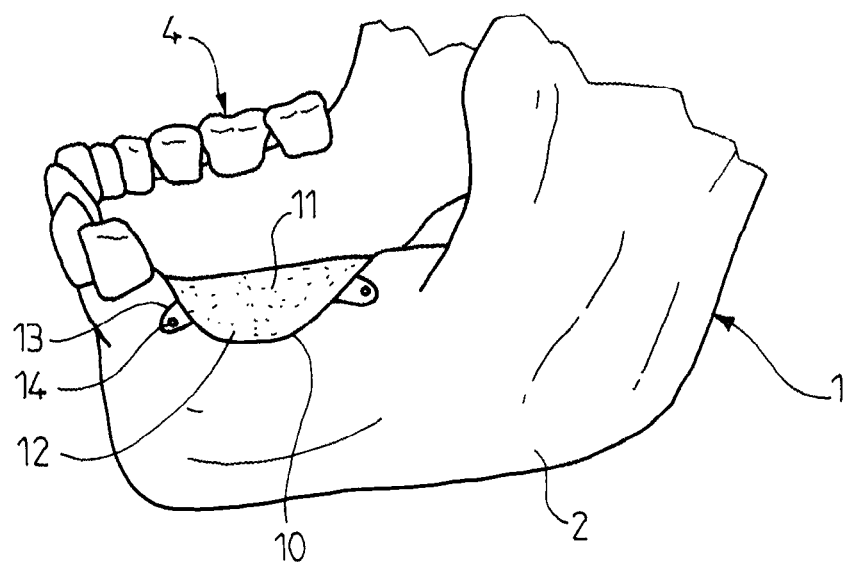
FIG. 5 is a view corresponding to FIG. 2 after placing and stabilizing the synthetic block according to the first embodiment of the invention.

The eyelets 13 are intended to abut against the respective side walls of the mandible as shown on FIG. 5. They each comprise a hole 14 for passing an osteosynthesis screw allowing to stabilize the part 11 when placed within the defect 10. The axis of the holes 14 is oriented so as to provide the desired orientation to the osteosynthesis screws in order to fix the eyelets 13 for a perfect stabilization of the part 11. Also, the eyelets 13 are positioned on the body 12 of the part 11 to ensure such stabilization.

Figure 6:
FIG. 6 is a view corresponding to FIG. 5 after resorbing the material of the synthetic block and replacing it with the patient's bone and placing artificial roots.

On FIG. 6 is shown the mandible 1 after resorbing of the ceramic material of the part 11 and replacing it with the patient's bone. After healing, the positioning of dental implants 15 is made possible.

The structure of the part 11 will be described below in reference to FIG. 13.

FIGS. 7 to 10 correspond to the views 1,2,5 and 6, respectively, for a maxilla 16:

FIG. 7 shows a front view of the maxilla 16 bearing the teeth 17 of the upper dental arch;

FIG. 8 shows the corresponding front view with loss of the four incisors and bone loss, creating the bone defect 18;

FIG. 9 shows the ceramic material part 19 according to the invention which body 20 fills in the bone defect and the eyelets 22 abut against the front wall of the maxilla, allowing osteosynthesis screws to pass through the corresponding holes 22; and FIG. 10 shows the front view of the maxilla after complete bone healing and placing the four dental implants on which the new teeth 24 have been placed.

FIGS. 11 and 12 are views corresponding to FIGS. 3 and 4, respectively, but with another embodiment of the means for stabilizing the part 11.

In this embodiment, through holes or bores 25 are pierced through the part 11 (two bores 25 in the example shown) for passing the osteosynthesis screw 26 (shown on FIGS. 11 and 12) to penetrate the patient's bone delimited by the bone defect 10. On the other side, each bore 25 flares along a chamfer part 27 for accommodating the corresponding screw head 28. The positioning and orientation of the axes of the screws 26 are selected to ensure a good stabilization of the part 11 for a successful revascularization.

If referring to FIG. 11, it can be noted that the part 11 can have two types of "porosity", namely:

a main part 11a in which the three-dimensional network of revascularization channels is composed of square-section channels, for example, with a 250-600 μm side+/−200 μm; and a surface part 11b which is not provided with a revascularization network, thus without channels (with only the microporosity) for a better resistance.

As indicated above, the part 11a could have a network more dense or with larger channel sections in its region in contact with the patient's bone for an acceleration of the revascularization.

FIGS. 14 and 15 show a part 11 consistent with the second embodiment, which has three different regions regarding its "porosity":

a core part 11A in which the three-dimensional network of revascularization channels is composed of square-section channels, for example, with a 250-350 μm side+/−200 μm;

a part 11B intended to come into contact with the patient's bone, in which the three-dimensional network of vascularization channels is more dense or is composed of square-section channels with a section larger than the channels of the part 11A, for example, with a 400-600 μm side+/−200 μm; and a surface part 11C surrounding the bores 25, which is not provided with a revascularization network, thus without channels (with only the microporosity) for a better resistance.

The structure according to the invention can be obtained according to any manufacturing method, layer by layer of the ceramic material.

The rapid prototyping and, in particular, the stereolithography are examples of such methods. This method is known by the man skilled in the art and, for a detailed description, reference can be made to U.S. Pat. No. 5,496,682 and EP1472081 patents.

Briefly, in pasty stereolithography, a paste is prepared, having for example the following composition (% of the total mass):

| | |
|---|---|
| ceramic | 80 |
| photocurable binder | 11.51 |
| photoinitiator | 0.09 |
| dispersant | 1.1 |
| plasticizer | 7.3 |

Here, the ceramic is hydroxyapatite or β-TCP or a mixture thereof. The photocurable binder can be an acrylate resin, such as di-ethoxylated A-bisphenol dimethacrylate or 1,6-hexanediol diacrylate. The photoinitiator will be selected among the photoinitiators commonly used in polymerization of acrylates. In particular, it can be noted 2,2'-dimethoxy-2-penylacetophenone and 2-hydroxy-2-methyl-1-phenyl-propane-1-one. The dispersant is advantageously a phosphoric ester. As a plasticizer, one or more agents of the group constituted by the family of glycols (for example, polyethylene glycol), the family of phthalates (for example, dibutylphthalate) and glycerol can be selected.

In a pasty stereolithography apparatus, the paste is first spread on a platform to form a first layer with uniform thickness. This first layer is irradiated by laser scanning according to the pattern defined for the layer. The first paste layer is cured by photopolymerization of the paste, except in the areas corresponding to the channels, which are not irradiated by the laser. Then, a second paste layer is spread on the first cured layer. This second layer is irradiated by laser scanning according to the pattern defined for the layer. The second paste layer is then cured, by photopolymerization of the paste, except in the areas corresponding to the channels. These operations are repeated in order to form the next stages.

Each of the layers formed has a thickness of 25-100 μm, namely 50 μm; it is obvious that the number of layers depends on the part being manufactured.

After photopolymerization of the last layer, the green part thus formed is cleaned to remove the non-polymerized composition. The cleaned green part is subjected to a heat treatment (debinding) and then to a sintering.

It is obvious that the above-described embodiments are provided for indicative and non-limiting purposes, and that modifications can be made without departing from the scope of the present invention.

The invention claimed is:

1. A synthetic block intended for filling in a bone defect at the surface of a bone, wherein the synthetic block is made up of a ceramic material part obtained by stereolithography and which has a shape allowing the synthetic block to fill in the bone defect and which is able to be stabilized when placed within the bone defect, an ordered three-dimensional network of revascularization channels communicating with one another being at least partially formed within the ceramic material part for allowing through the fluids and cells that enable revascularization for cell growth once the ceramic material part is placed within the bone defect, the channels opening onto each surface of the bone defect in contact with the ceramic material part once the synthetic block is placed within the bone defect,
wherein the ceramic part is pierced with at least one through hole, from the surface intended to come into contact with the bone delimiting the bone defect to the free surface if one considers the position of the part placed within the bone defect, for passing at least one stabilization screw, the ceramic part being not provided with revascularization channels within the regions surrounding the through hole at least in the neighboring part of the free surface.

2. The synthetic block according to claim 1, wherein the ceramic material is one of a ceramic material which is at least partially resorbable and a non-resorbable ceramic material.

3. The synthetic block according to claim 1, wherein the ceramic material is selected among β-tricalcium phosphate (β-TCP), hydroxyapatite and mixtures thereof in any proportion.

4. The synthetic block according to claim 1, wherein the ceramic material is a mixture composed of, for 100 wt. %, 40-100 wt. % of hydroxyapatite and 0-60 wt. % of β-TCP.

5. The synthetic block according to claim 1, wherein the ceramic part externally has, integral therewith, at least one stabilization eyelet intended to abut against the surface of the bone to be restored, outside the bone defect, the stabilization eyelet being not provided with revascularization channels and being pierced with at least one hole for passing at least one stabilization screw.

6. The synthetic block according to claim 1, wherein the ceramic part externally has, integral therewith, at least one stabilization eyelet intended to abut against the surface of the bone to be restored, outside the bone defect, the stabilization eyelet being not provided with revascularization channels and being pierced with at least one hole for passing at least one stabilization screw and wherein the ceramic part is pierced with at least one through hole, from the surface intended to come into contact with the bone delimiting the bone defect to the free surface if one considers the position of the part placed within the bone defect, for passing at least one stabilization screw, the ceramic part being not provided with revascularization channels within the regions surrounding the through hole at least in the neighbouring part of the free surface.

7. The synthetic block according to claim 1, wherein the part is not provided with revascularization channels within the region of its free surface if one considers the position of the part placed within the bone defect.

8. The synthetic block according to claim 1, wherein the revascularization channels have a variable section, are rectilinear or not, and open or not at the opposite side of the surface of the part intended to come into contact with the bone defect.

9. The synthetic block according to claim 1, wherein the channels forming the revascularization system have a side of 250-600 μm with a 200 μm tolerance.

10. The synthetic block according to claim 1, wherein a cross-section of the revascularization channels which are located within one or more regions of the ceramic material part intended to contact the bone delimiting the bone defect is greater than a cross-section of the revascularization channels which are located in a core of the ceramic material part.

11. The synthetic block according to claim 10, wherein the channels of a greater cross-section are square-shaped in cross-section with a 400-600 μm side and with a 200 μm tolerance.

12. The synthetic block according to claim 1, wherein a density of the channels forming the revascularization system is higher within one or more regions of the part intended to contact the bone defect.

13. A method for manufacturing a synthetic block as defined in claim 1, wherein the method comprises the following steps:
acquiring a three-dimensional image of a patient's bone having the bone defect to be filled in;
designing, by computer-aided design, a computing model of the synthetic block which shape corresponds to the bone defect, which has the revascularization channels and which sizes are slightly larger than the bone defect so as to take into account the shrinkage of the ceramic when manufacturing the synthetic block;

changing this computing model of the synthetic block, by computer-aided design, to ensure the stabilization of the synthetic block within the bone defect; and manufacturing the desired synthetic block by stereolithography or 3D printing or technique of additive methods.

14. A synthetic block intended for filling in a bone defect at the surface of a bone, wherein the synthetic block is made up of a ceramic material part obtained by stereolithography and which has a shape allowing the synthetic block to fill in the bone defect and which is able to be stabilized when placed within the bone defect, an ordered three-dimensional network of revascularization channels communicating with one another being at least partially formed within the ceramic material part for allowing through the fluids and cells that enable revascularization for cell growth once the ceramic material part is placed within the bone defect, the channels opening onto each surface of the bone defect in contact with the ceramic material part once the synthetic block is placed within the bone defect, wherein the ceramic material constituting the part has an intergranular microporosity of 5-30% in volume, the micropores having a size of 0.1-10 µm.

15. The synthetic block according to claim 14, wherein the ceramic material is one of a ceramic material which is at least partially resorbable and a non-resorbable ceramic material.

16. The synthetic block according to claim 14, wherein the ceramic material is selected among β-tricalcium phosphate (β-TCP), hydroxyapatite and mixtures thereof in any proportion.

17. The synthetic block according to claim 14, wherein the ceramic material is a mixture composed of, for 100 wt. %, 40-100 wt. % of hydroxyapatite and 0-60 wt. % of β-TCP.

18. The synthetic block according to claim 14, wherein the ceramic part externally has, integral therewith, at least one stabilization eyelet intended to abut against the surface of the bone to be restored, outside the bone defect, the stabilization eyelet being not provided with revascularization channels and being pierced with at least one hole for passing at least one stabilization screw.

19. The synthetic block according to claim 14, wherein the ceramic part externally has, integral therewith, at least one stabilization eyelet intended to abut against the surface of the bone to be restored, outside the bone defect, the stabilization eyelet being not provided with revascularization channels and being pierced with at least one hole for passing at least one stabilization screw and wherein the ceramic part is pierced with at least one through hole, from the surface intended to come into contact with the bone delimiting the bone defect to the free surface if one considers the position of the part placed within the bone defect, for passing at least one stabilization screw, the ceramic part being not provided with revascularization channels within the regions surrounding the through hole at least in the neighbouring part of the free surface.

20. The synthetic block according to claim 14, wherein the part is not provided with revascularization channels within the region of its free surface if one considers the position of the part placed within the bone defect.

21. The synthetic block according to claim 14, wherein the revascularization channels have a variable section, are rectilinear or not, and open or not at the opposite side of the surface of the part intended to come into contact with the bone defect.

22. The synthetic block according to claim 14, wherein the channels forming the revascularization system have a side of 250-600 µm with a 200 µm tolerance.

23. The synthetic block according to claim 14, wherein a cross-section of the revascularization channels which are located within one or more regions of the ceramic material part intended to contact the bone delimiting the bone defect is greater than a cross-section of the revascularization channels which are located in a core of the ceramic material part.

24. The synthetic block according to claim 14, wherein the channels of a greater cross-section are square-shaped in cross-section with a 400-600 µm side and with a 200 µm tolerance.

25. The synthetic block according to claim 14, wherein a density of the channels forming the revascularization system is higher within the one or more regions of the part intended to contact the bone defect.

26. A method for manufacturing a synthetic block as defined in claim 14, wherein the method comprises the following steps:

acquiring a three-dimensional image of a patient's bone having the bone defect to be filled in;

designing, by computer-aided design, a computing model of the synthetic block which shape corresponds to the bone defect, which has the revascularization channels and which sizes are slightly larger than the bone defect so as to take into account the shrinkage of the ceramic when manufacturing the synthetic block;

changing this computing model of the synthetic block, by computer-aided design, to ensure the stabilization of the synthetic block within the bone defect; and manufacturing the desired synthetic block by stereolithography or 3D printing or technique of additive methods.

* * * * *